United States Patent [19]

Nelson et al.

[11] 4,112,114
[45] Sep. 5, 1978

[54] ESTERS OF 2-SUBSTITUTED-5-OXO-5H-DIBENZO[A,D-]CYCLOHEPTENES HAVING PHARMACEUTICAL ACTIVITY, AND METHODS AND COMPOSITIONS FOR THE USE THEREOF

[75] Inventors: Peter H. Nelson; Karl G. Untch, both of Los Altos, Calif.

[73] Assignee: Syntex (U.S.A.) Inc., Palo Alto, Calif.

[21] Appl. No.: 830,264

[22] Filed: Sep. 2, 1977

Related U.S. Application Data

[62] Division of Ser. No. 724,042, Sep. 16, 1976, abandoned, which is a division of Ser. No. 619,158, Oct. 3, 1975, abandoned.

[51] Int. Cl.² .................................... C07D 317/36
[52] U.S. Cl. ...................... 424/285; 260/340.2; 560/71; 260/340.9 R; 260/348.59
[58] Field of Search .................... 260/340.2

[56] References Cited

U.S. PATENT DOCUMENTS 4,020,094   4/1977   Nelson et al. .................. 260/469

*Primary Examiner*—Norma S. Milestone
*Attorney, Agent, or Firm*—Alan M. Krubiner

[57] ABSTRACT

Esters of 2-substituted-5-oxo-5H-dibenzo[a,d]cycloheptenes represented by the following formula:

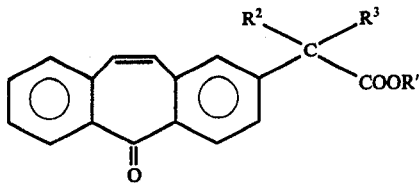

where R′ is —CH$_2$—CH=CH$_2$, —CH$_2$—CH(OH)—CH$_2$OH,

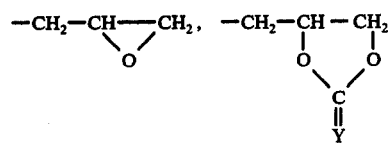

where Y is either O or S, or

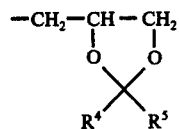

where R$^4$ and R$^5$ are independently hydrogen, alkyl having 1 to 6 carbon atoms, phenyl, or benzyl, or together R$^4$ and R$^5$ form an alkylene bridge having 4, 5 or 6 carbon atoms; one of R$^2$ and R$^3$ is hydrogen and the other is hydrogen, methyl, or ethyl, or together R$^2$ and R$^3$ are methylene. The compounds have anti-inflammatory, analgesic, and antipyretic activities and, accordingly, are useful in the treatment of inflammation, pain and/or pyrexia.

4 Claims, No Drawings

ESTERS OF 2-SUBSTITUTED-5-OXO-5H-DIBENZO[A,D]CYCLOHEPTENES HAVING PHARMACEUTICAL ACTIVITY, AND METHODS AND COMPOSITIONS FOR THE USE THEREOF

CROSS-REFERENCE TO RELATED APPLICATION

This is a division of application Ser. No. 724,042, filed Sept. 16, 1976, abandoned which in turn is a division of Ser. No. 619,158, filed Oct. 3, 1975, abandoned.

The esters described in this application are related to the acids described in application Ser. No. 561,517, filed Mar. 24, 1975 and now U.S. Pat. No. 4,020,094.

FIELD OF THE INVENTION

This invention relates to novel chemical compounds. More particularly, this invention relates to esters of 5-oxo-5H-dibenzo[a,d]cycloheptene derivatives substituted at the 2-position with an acetic moiety or an α-substituted acetic acid moiety.

SUMMARY OF THE INVENTION

The esters of the 2-substituted 5-oxo-5H-dibenzo[a,d]-cycloheptenes of the present invention can be represented by the following formula:

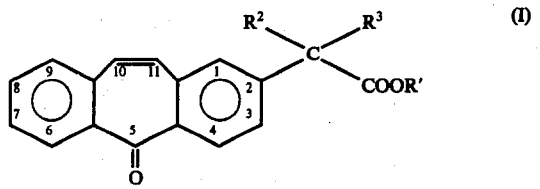

where R' is —CH$_2$—CH=CH$_2$, —CH$_2$—CH(OH)—CH$_2$OH,

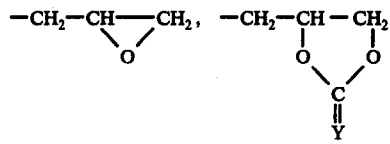

where Y is either O or S, or

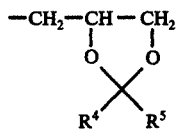

where R$^4$ and R$^5$ are independently hydrogen, alkyl having 1 to 6 carbon carbon atoms, phenyl, or benzyl, or together R$^4$ and R$^5$ form an alkylene bridge having 4, 5 or 6 carbon atoms; one of R$^2$ and R$^3$ is hydrogen and the other is hydrogen, methyl, or ethyl, or together R$^2$ and R$^3$ are methylene.

As used in this specification and claims, the term "alkyl" refers to both straight and branched alkyl groups having from 1 to 6 carbon atoms, and thus includes primary, secondary and tertiary alkyl groups. Typical alkyls include for example, methyl, ethyl, n-propyl, isopropyl, n-butyl, isobutyl, t-butyl, n-amyl, n-hexyl, and the like.

When one of R$^2$ and R$^3$ is hydrogen and the other is methyl or ethyl, and/or R' is as set forth above with the exception of —CH$_2$—CH=CH$_2$, and/or R$^4$ and R$^5$ are different, the compounds of Formula I exist as mixtures of diastereomers (i.e., pairs of enantimorphs). Each enantiomorph or optical isomer and mixtures thereof are included within the present invention. The compounds of Formula I which exist as pairs of enantiomorphs can be administered as mixtures of enantiomorphs or as resolved enantiomorphs. In some instances, one enantiomorph or enantiomeric pair may exhibit greater anti-inflammatory, analgesic and/or anti-pyretic activity than the other corresponding enantiomorph or enantiomeric pair.

The compounds of Formula I exhibit anti-inflammatory, analgesic and anti-pyretic activities. Accordingly, the compositions of this invention are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the compounds of this invention are useful for the relief of these conditions as well as the inflammation.

Administration of the active compounds of Formula I in an appropriate pharmaceutical composition can be via any of the accepted modes of administration of agents for the treatment of inflammation, pain, or pyrexia. Thus, administration can be, for example, orally, parenterally, or topically, in the form of solid, semi-solid or liquid dosage forms, such as, for example, tablets, suppositories, pills, capsules, powders, liquid solutions, suspensions, creams, lotions, ointments, or the like, preferably in unit dosage forms suitable for simple administration of precise dosages. The compositions of this invention will include a conventional pharmaceutical carrier or excipient and an active compound of Formula I, and, in addition, may include other medicinal agents, pharmaceutical agents, carriers, adjuvants, etc.

The preferred manner of administration is oral using a convenient daily dosage regimen which can be adjusted according to the degree of affliction. Generally, a daily dose of from 0.05 mg. to 20 mg. of active compound of Formula I per kilogram of body weight is used. Most conditions respond to treatment comprising a dosage level of the order of 0.5 mg. to 5 mg. per kilogram of body weight per day. For such oral administration, a pharmaceutically acceptable non-toxic composition is formed by the admixture of a compound of Formula I with any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compound of Formula I may be formulated into a suppository using, for example, polyalkylene glycols, for example, polypropylene glycol, as the carrier. Liquid pharmaceutically administerable compositions can, for example, be prepared by dissolving, dispersing, etc. an active compound of Formula I and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifing agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's *Pharmaceutical Sciences*, Mack Publishing Company, Easton, Pennsylvania, 14th Edition, 1970. The composition to be administered will, in any event, contain a quantity of the active compound(s) in a pharmaceutically effective amount for relief of the particular condition being treated in accordance with the teachings of this invention.

The compounds of Formula I are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

The compounds of Formula I are also used as agents for delaying the onset of, or for postponing, parturition. As used in this application, the phrase "to delay the onset of parturition" is intended to cover that delay in parturition caused by the administration of a compound of Formula I at any time before uterine muscle contactions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time considered favorable to the mother and/or fetus.

As used in this application, the phrase "postponing parturition" is intended to cover that delay in parturition caused by the administration of a compound of Formula I after uterine muscle contractions have begun. The condition of the patient, including the time within the gestation period when the contractions have begun, the severity of the contractions and how long the contractions have taken place will affect the results achieved with the administration of a compound of Formula I. For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

With respect to animals, this treatment can also be utilized to synchronize the deliveries from a group of pregnant animals to happen at or about the same time, or to happen at or about a desired time and/or place, when the births can be handled with greater facility.

In all cases, administration of the compounds of Formula I for the purposes should be consistent with best and/or accepted medical (or veterinary) practices so as to maximize the benefits to the mother and the fetus. For example, administration should not be continued so long past full term that the fetus dies in utero.

In the practice of this aspect of the present invention, a therapeutically effective amount of a compound of Formula I or a pharmaceutical composition containing a compound of Formula I is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally or parenterally in the doses and in the forms (including oral, vaginal or uterine tablets or suppositories, etc.) as set forth above regarding anti-inflammatory, etc. activities. Administration can be a single daily dose or up to 3 or 4 smaller doses regularly given throughout the day. The actual amount of active compound administered will, of course, depend on its relative activity for this particular utility.

The compounds of Formula I can be prepared by esterification according to known procedures, for example, by the reaction of a suitable alcohol with (a) the free acid [i.e., (5-oxo-5H-dibenzo[a,d]cyclohepten-2-yl)acetic acid or an $R^2/R^3$-substituted derivative thereof as described herein] in the presence of an acidic catalyst or a dehydrating catalyst at temperatures in the range from room temperature to the reflux temperature of the solvent utilized or (b) one of the functional derivatives of the free acid, such as (i) the acid halide, such as, for example, the acid chloride, in the presence of a tertiary nitrogenous base at a temperature in the range from $-80°$ C to the reflux temperature of the solvent utilized or (ii) the acid anhydride of the formula

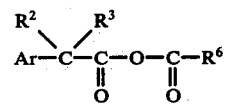

where Ar is (5-oxo-5H-dibenzo[a,d]cyclohepten-2-yl), $R^2$ and $R^3$ are as defined hereinabove, and $R^6$ is Ar, alkyl ($C_{1-20}$) optionally substituted with halogen (fluoro, chloro or bromo), or aryl ($C_{6-10}$) optionally substituted with halogen, alkyl ($C_{1-6}$), nitro, or cyano, at a temperature in the range of $-80°$ C to the reflux temperature of the solvent utilized. Other methods of esterification or transesterification, and other transformations of prepared esters, known to those skilled in this art can also be utilized. For example, the compounds of Formula I can be prepared by (a) selective acid hydrolysis of an ester of Formula I having a conventional ketal protecting group at either the 5-position and/or in the ester portion thereof, in the presence of a mild mineral or organic acid (e.g., aqueous hydrochloric acid, aqueous sulfuric acid, aqueous acetic acid, aqueous chloroacetic acid, and the like) at a temperature in the range from room temperature to the reflux temperature of the solvent utilized, or (b) transesterification of a compound of Formula I with a suitable alcohol to afford a different compound of Formula I or transesterification of a compound represented by the Formula

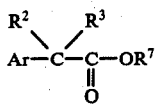

where Ar, $R^2$ and $R^3$ are as defined hereinabove, and $R^7$ is alkyl ($C_{1-20}$), preferably alkyl ($C_{1-4}$), also with a suitable alcohol. Transesterification, as set forth above, is conducted in the presence of an acidic catalyst at a temperature in the range from room temperature to the reflux temperature of the solvent utilized. Suitable alcohols include allyl alcohol; 2,3-epoxypropan-1-ol; 4-hydroxymethyl-2,2-dimethyl-1,3-dioxolane, and the like; and suitable solvents include the aforementioned alcohols with or without an inert co-solvent, such as for example, benzene, toluene, tetrahydrofuran, monoglyme, diglyme, and the like. Optionally, the compounds of Formula I where one of $R^2$ and $R^3$ is hydrogen and the other is methyl or ethyl, or together $R^2$ and $R^3$ are methylene, and R' is other than —$CH_2$—CH(OH)—$CH_2OH$ or

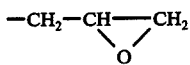

can be prepared by introducing an α-methyl, α-ethyl or α,α-methylene group on an ester of Formula I where both $R^2$ and $R^3$ are hydrogen and R' is other than —$CH_2$—CH(OH)—$CH_2OH$ or

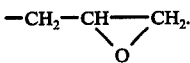

The aforesaid ester starting material is treated with an alkali metal hydride, amide or dialkylamide, sodium hydride, lithium diisopropylamide or sodium methylamide, followed by treatment with an alkyl halide, such as methyl iodide or ethyl iodide, or dialkyl sulfate (e.g., dimethyl sulfate or diethyl sulfate) to α-alkylate the ester starting material. These reactions can be conducted in tetrahydrofuran, monoglyme, diglyme, hexamethylphosphoramide, or mixtures thereof, at a temperature in the range from −80° C to reflux temperature of the solvent. The α,α-methylene group is introduced by treating the ester starting material with an alkali metal dialkylamide, such as lithium diisopropylamide, in tetrahydrofuran, monoglyme, diglyme or hexamethylphosphoramide, or mixtures thereof, followed by the addition of formaldehyde, at a temperature in the range from −80° C to the reflux temperature of the solvent.

The preparation of 2-(5-oxo-5H-dibenzo[a,d]cyclohepten-2-yl)propionic acid, the optical isomers thereof, 2-(5-oxo-5H-dibenzo[a,d]cyclohepten-2-yl)propionyl chloride, (5-oxo-5H-dibenzo[a,d]cyclohepten-2-yl)acetic acid, (5-oxo-5H-dibenzo[a,d]-cyclohepten-2-yl)acetyl chloride, 2-(5-oxo-5H-dibenzo[a,d]cyclohepten-2-yl)butyric acid, and 2-(5-oxo-5H-dibenzo[a,d]cyclohepten-2-yl)acrylic acid, are given in copending application Ser. No. 561,517, filed Mar. 24, 1975. The disclosure thereof, particularly those portions thereof dealing with the preparation of the compounds listed herein above, is incorporated herein by reference.

The use of the symbol "R" or "S" preceding a substituent in the alcohol portion of the ester designates the absolute stereochemistry of that substituent according to the Cahn-Ingold-Prelog rules [see Cahn et al., *Angew. Chem. Inter.* Edit., Vol. 5, p. 385 (1966), errata p. 511; Cahn et al., *Angew. Chem.*, Vol. 78 p. 413 (1966); Cahn and Ingold, *J. Chem. Soc.*, (London), 1951, p. 612; Cahn et al., *Experientia*, Vol. 12, p. 81 (1956); Cahn, *J. Chem. Educ.*, Vol. 41, p. 116 (1964)].

Exemplary of the compounds of the present invention, as represented by the structural formula above, are the following illustrative compounds:

allyl (5-oxo-5H-dibenzo[a,d]cyclohepten-2-yl)acetate;
allyl 2-(5-oxo-5H-dibenzo[a,d]cyclohepten-2-yl)propionate;
allyl 2-(5-oxo-5H-dibenzo[a,d]cyclohepten-2-yl)butyrate;
allyl 2-(5-oxo-5H-dibenzo[a,d]cyclohepten-2-yl)acrylate;
2',3'-dihydroxyprop-1'-yl (5-oxo-5H-dibenzo[a,d]cyclohepten-2-yl)acetate;
2',3'-dihydroxyprop-1'-yl 2-(5-oxo-5H-dibenzo[a,d]cyclohepten-2-yl)propionate;
2',3'-dihydroxyprop-1'-yl 2-(5-oxo-5H-dibenzo[a,d]cyclohepten-2-yl)butyrate;
2',3'-dihydroxyprop-1'-yl 2-(5-oxo-5H-dibenzo[a,d]cyclohepten-2-yl)acrylate;
2',3'-epoxyprop-1'-yl (5-oxo-5H-dibenzo[a,d]cyclohepten-2-yl)acetate;
2',3'-epoxyprop-1'-yl 2-(5-oxo-5H-dibenzo[a,d]cyclohepten-2-yl)propionate;
2',3'-epoxyprop-1'-yl 2-(5-oxo-5H-dibenzo[a,d]cyclohepten-2-yl)butyrate;
2',3'-epoxyprop-1'-yl 2-(5-oxo-5H-dibenzo[a,d]cyclohepten-2-yl)acrylate;
(2-oxo-1,3-dioxolan-4-yl)methyl (5-oxo-5H-dibenzo[a,d]cyclohepten-2-yl)acetate;
(2-oxo-1,3-dioxolan-4-yl)methyl 2-(5-oxo-5H-dibenzo[a,d]cyclohepten-2-yl)propionate;
(2-oxo-1,3-dioxolan-4-yl)methyl 2-(5-oxo-5H-dibenzo[a,d]cyclohepten-2-yl)butyrate;
(2-oxo-1,3-dioxolan-4-yl)methyl 2-(5-oxo-5H-dibenzo[a,d]cyclohepten-2-yl)acrylate;
(2-thioxo-1,3-dioxalan-4-yl)methyl (5-oxo-5H-dibenzo[a,d]cyclohepten-2-yl)acetate;
(2-thioxo-1,3-dioxalan-4-yl)methyl 2-(5-oxo-5H-dibenzo[a,d]cyclohepten-2-yl)propionate;
(2-thioxo-1,3-dioxalan-4-yl)methyl 2-(5-oxo-5H-dibenzo[a,d]cyclohepten-2-yl)butyrate;
(2-thioxo-1,3-dioxalan-4-yl)methyl 2-(5-oxo-5H-dibenzo[a,d]cyclohepten-2-yl)acrylate;
(2,2-dimethyl-1,3-dioxolan-4-yl)methyl (5-oxo-5H-dibenzo-[a,d]cyclohepten-2-yl)acetate;
(2,2-dimethyl-1,3-dioxolan-4-yl)methyl 2-(5-oxo-5H-dibenzo[a,d]cyclohepten-2-yl)propionate;
(2,2-dimethyl-1,3-dioxolan-4yl)methyl 2-(5-oxo-5H-dibenzo-[a,d]cyclohepten-2-yl)butyrate;
(2,2-dimethyl-1,3-dioxolan-4-yl)methyl 2-(5-oxo-5H-dibenzo[a,d]cyclohepten-2-yl)acrylate;
(2-methyl-1,3-dioxolan-4-yl)methyl 2-(5-oxo-5H-dibenzo[a,d]cyclohepten-2-yl)propionate;

(2-hexyl-1,3-dioxolan-4-yl)methyl 2-(5-oxo-5H-dibenzo-[a,d]cyclohepten-2-yl)propionate;
(1,3-dioxolan-4-yl)methyl 2-(5-oxo-5H-dibenzo[a,d]cyclohepten-2-yl)propionate;
(2-phenyl-1,3-dioxolan-4-yl)methyl 2-(5-oxo-5H-dibenzo[a,d]cyclohepten-2-yl)propionate;
(2-benzyl-1,3-dioxolan-4-yl)methyl 2-(5-oxo-5H-dibenzo[a,d]cyclohepten-2-yl)propionate;
[2,2-(1,4-tetramethylene)-1,3-dioxolan-4-yl]methyl 2-(5-oxo-5H-dibenzo[a,d]cyclohepten-2-yl)propionate;
[2,2-(1,5-pentamethylene)-1,3-dioxolan-4-yl]methyl 2-(5-oxo-5H-dibenzo[a,d]cyclohepten-2-yl)propionate;
[2,2-(1,6-hexamethylene)-1,3-dioxolan-4-yl]methyl 2-(5-oxo-5H-dibenzo[a,d]cyclohepten-2-yl)propionate;
and the corresponding individual optical isomers or optical isomer pairs of those compounds which have one or more asymmetric carbon atoms.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

148 G. of 2-methylterephthalic acid is refluxed for 24 hrs. in 750 ml. of dry methanol containing 30 ml. of sulphuric acid. The solution is cooled, poured into water and extracted with ether. The extract is washed, dried and evaporated to give dimethyl-2-methylterephthalate.

88 G. of dimethyl-2-methylterephthalate in 1000 ml. of carbon tetrachloride containing 89 g. (1 eq.) of N-bromosuccinimide is refluxed for 3 hours using a heat lamp. The solution is cooled, filtered and evaporated to dryness to give dimethyl-2-bromomethylterephthalate.

25.7 G. of dimethyl-2-bromomethylterephthalate is refluxed in 250 ml. of acetonitrile containing 26.2 g. (1 eq.) of triphenylphosphine for 4 hrs. The solution is cooled and diluted with 1250 ml. of ether thereby precipitating 2,5-bis(carbomethoxy)-benzyltriphenylphosphonium bromide which is filtered off and dried under vacuum.

51.9 G. of 2,5-bis(carbomethoxy)-benzyltriphenylphosphonium bromide and 10.6 g. of benzaldehyde are stirred in 300 ml. of acetonitrile and 12.4 g. of diazabicyclononene is added. The mixture is heated briefly to reflux, then cooled and evaporated to an oil. The oil is dissolved in ethyl acetate, and the solution washed with dilute hydrochloric acid, dried and evaporated. The residue is refluxed for 12 hrs. in a solution of 20 g. of potassium hydroxide in 300 ml. of water and 50 ml. of methanol. The solution is cooled and extracted with chloroform. The aqueous solution is acidified with dilute hydrochloric acid and the precipitated cis and trans stilbene-2,5-dicarboxylic acids are filtered off and dried.

23.6 G. of cis and trans-stilbene-2,5-dicarboxylic acids are dissolved in 100 ml. of dimethylformamide containing 500 mg. of 5% palladium on carbon and hydrogenated for 2 hrs. The solution is filtered and evaporated to dryness to give a crude product which upon recrystallization from aqueous ethanol yields 2-(2-phenethyl)-terephthalic acid.

23.8 G. of 2-(2-phenethyl)terephthalic acid is dissolved in 200 ml. of sulpholane at 130° C and 150 ml. of polyphosphoric acid is added with stirring. The mixture is stirred at 130° C for 4 hrs., then poured into 1000 ml. of water. The product is filtered off and recrystallized from aqueous dimethylformamide to yield 5-oxo-5H-dibenzo[a,d]-cycloheptane-2carboxylic acid.

PREPARATION 2

5.0 G. of 5-oxo-5H-dibenzo[a,d]cycloheptane-2-carboxylic acid (as prepared in Preparation 1 above) is suspended in 50 ml. of dioxane, added to excess ethereal diazomethane, and stirred until dissolution is complete. The solution is then evaporated to dryness to yield 2-carbomethoxy-5-oxo-5H-dibenzo[a,d]cycloheptane. Hydrolysis 4.68 G. of 2-carbomethoxy-5-oxo-5H-dibenzo[a,d]cycloheptane is refluxed in 100 ml. of carbon tetrachloride containing 3.56 g. (1 eq.) of N-bromosuccinimide while being irradiated with a 100 watt incandescent lamp. After 2 hrs. the solution is cooled, filtered and evaporated to dryness. The residue is dissolved in 30 ml. of dimethylformamide and 2.48 g. (1 eq.) of diazbicyclononene is added. The mixture is heated briefly to 60° C, and water and ethyl acetate are added. The organic layer is washed with dilute hydrochloric acid and water, then dried and evaporated to give 2-carbomethoxy-5-oxo-5H-dibenzo[a,d]cycloheptene. Hydrolysis in eight to one aqueous methanol, 5% potassium hydroxide, followed by acidification with dilute hydrochloric acid yields 5-oxo-5H-dibenzo[a,d]cycloheptene-2-carboxylic acid.

PREPARATION 3

22 G. of 5-oxo-5H-dibenzo[a,d]cycloheptene-2-carboxylic acid is stirred in 200 ml. of chloroform, 50 ml. of thionyl chloride and 1 ml. of dimethylformamide for 8 hours. The mixture is evaporated to dryness and the residue recrystallized from acetonitrile to yield 2-chloroformyl-5-oxo-5H-dibenzo[a,d]cycloheptene.
This is dissolved in 200 ml. of chloroform and added to a 3-fold excess of ethereal diazomethane at 0° C. The mixture is left at 0° C for 12 hrs. then evaporated to dryness. The residue is recrystallized from acetonitrile to yield 2-diazoacetyl-5-oxo-5H-dibenzo[a,d]cycloheptene. The diazoketone is heated to reflux in 250 ml. of ethanol and a saturated triethylamine solution of 2 g. of silver benzoate is added slowly until gas evolution ceases. The solution is cooled, filtered and evaporated to yield ethyl (5-oxo-5H-dibenzo[a,d]cyclohepten-2-yl)acetate. This ester is refluxed in 5% aqueous potassium hydroxide for 12 hrs. The solution is cooled, acidified with dilute hydrochloric acid and extracted with ether. The ether extract is dried and evaporated to yield (5-oxo-5H-dibenzo[a,d]cyclohepten-2-yl)acetic acid which can be recrystallized from acetone-hexane.

PREPARATION 4

Lithium isopropylcyclohexylamide is prepared by adding 10 mls. of 1.0 molar n-butyl lithium to a solution of 1.41 g. of isopropylcyclohexylamine in 100 ml. of dry tetrahydrofuran. To this solution, cooled to −80° C, there is added a solution of 2.94 g. of ethyl (5-oxo-5H-dibenzo[a,d]cyclohepten-2-yl)acetate (as prepared in Preparation 3 above) in 10 ml. of tetrahydrofuran. The mixture is left for 5 minutes, then 1.42 g. of methyl iodide is added. The reaction mixture is allowed to attain room temperature, then water and ether are added. The ethereal layer is washed with dilute hydrochloric acid and water, dried and evaporated to yield ethyl 2-(5-oxo-5H-dibenzo[a,d]cyclohepten-2-yl)propionate. This ethyl ester is refluxed for 12 hrs. in 5% aqueous potassium hydroxide, followed by acidification with dilute hydrochloric acid and ether extraction to afford 2-(5-oxo-5H-dibenzo[a,d]cyclohepten-2-yl)propionic acid.

PREPARATION 5

1.075 Ml. of 1.6 molar n-butyllithium in hexane is added to a solution of 0.242 ml. of diisopropylamine in 15 ml. of dry tetrahydrofuran. 0.300 Ml. of hexamethylphosphoric triamide is added and the mixture is cooled to about −60° C. 0.465 G. of methyl (5-oxo-5H-dibenzo[a,d]-cyclohepten-2-yl)acetate is added, and after 15 minutes, 0.137 ml. of ethyl iodide is added. The mixture is warmed slowly to room temperature and a further 0.05 ml. of ethyl iodide is added. After 30 minutes an additional 0.05 ml. of ethyl iodide is added. After 30 minutes, a few drops of methanol are added, and then ether and water are added. The organic layer is washed with water, dilute hydrochloric acid and saturated sodium chloride solution, then dried and evaporated to yield the impure product, which, after chromatography on 40 g. silica gel, eluting with hexane:ether (5:1) affords methyl 2-(5-oxo-5H-dibenzo[a,d]cyclohepten-2-yl)butyrate. 0.326 G. of methyl 2-(5-oxo-5H-dibenzo[a,d]cyclohepten-2-yl)butyrate is refluxed for 4 hours in 10 ml. of methanol and 20 ml. of water containing 0.5 g. of sodium hydroxide. The mixture is cooled, washed with ether and acidified with dilute hydrochloric acid. The product is extracted with ether and the extract washed, dried and evaporated to yield 2-(5-oxo-5H-dibenzo[a,d]cyclohepten-2-yl)butyric acid.

PREPARATION 6

1.25 Ml. of 1.6 molar n-butyllithium in hexane is added to a solution of 0.280 ml. of diisopropylamine in 30 ml. of tetrahydrofuran. The solution is cooled to −80° C and 0.556 g. of methyl (5-oxo-5H-dibenzo[a,d]cyclohepten-2-yl)acetate is added. After 10 minutes 0.38 ml. of hexamethylphosphoric triamide is added. The cooling bath is removed and formaldehyde vapor, entrained in nitrogen, is passed over the solution until it becomes colorless. Water and ether are then added and the organic layer is washed with dilute hydrochloric acid, saturated sodium chloride solution, then dried and evaporated. The residue is chromatographed on 10 g. of silica gel, eluting with hexane:ethyl acetate (5:1) to isolate methyl 2-(5-oxo-5H-dibenzo-[a,d]cyclohepten-2-yl)acrylate. 0.02 G. of this compound is refluxed under nitrogen in 5 ml. of water, 2 ml. of ethanol and 0.5 ml. of saturated sodium carbonate solution for 4 hours. The mixture is cooled, washed with ether and acidified with dilute hydrochloric acid, then extracted with ethyl acetate and the extract dried and evaporated to yield 2-(5-oxo-5H-dibenzo[a,d]cyclohepten-2-yl)acrylic acid.

PREPARATION 7

2.78 G. (0.01 mole) of 2-(5-oxo-5H-dibenzo[a,d]cyclohepten-2-yl)propionic acid is dissolved in 25 ml. of isopropanol and 1.35 g. (0.01 mole) of l-amphetamine is added. The salt crystallizes out and is filtered off and recrystallized several times to constant specific rotation. The salt is suspended in ether and dilute hydrochloric acid is added. After shaking, the organic layer is washed, dried and evaporated to give d 2-(5-oxo-5H-dibenzo[a,d]cyclohepten-2-yl)propionic acid, $[\alpha]_D$ + 48.9° (chloroform), which can be recrystallized from acetone-hexane. l 2-(5-Oxo-5H-dibenzo[a,d]cyclohepten-2-yl)propionic acid can be obtained in similar manner using d-amphetamine.

PREPARATION 8

2.78 G. of 2-(5-oxo-5H-dibenzo[a,d]cyclohepten-2-yl)propionic acid is stirred in a mixture of 20 ml. of benzene and 5 ml. of trifluoroacetic anhydride for 15 minutes. The mixture is evaporated to dryness and redissolved in 20 ml. of dry benzene. A mixture of 1.0 g. of pyridine and 2.44 g. (2 moles) of (+) α-phenylethanol is added. The mixture is left for 30 minutes and then water and ether is added. The organic layer is washed with dilute hydrochloric acid and water, then dried and evaporated. The residue is chromatographed on 100 g. silica gel, eluting with hexane:ether (4:1) to afford a 1:1 mixture of diastereomeric esters. Repeated crystallization of this mixture from ether-hexane yields the less soluble isomer. The purity of samples from successive recrystallizations is monitored by gas-liquid chromatography using a 1 meter × 2 mm. column packed with Chromosorb W (Regis Chemical Co., Chicago, Ill.) impregnated with 3% w/w OV101 polymeric material (Applied Sciences Laboratory, Inc., State College, Penn.) as stationary phase, and helium as the carrier gas at 220° C. The less soluble isomer is decomposed by stirring in a mixture of 5 ml. of benzene and 5 ml. of trifluoroacetic acid for 30 minutes. Water and ether are added and the ethereal layer washed with water, and then with dilute aqueous sodium carbonate. The aqueous layer is acidified with dilute hydrochloric acid and then extracted with ether. The ethereal layer is washed, dried and evaporated to give d 2-(5-oxo-5H-dibenzo[a,d]cyclohepten-2-yl)propionic acid. l 2-(5-Oxo-5H-dibenzo[a,d]cyclohepten-2-yl)propionic acid, $[\alpha]_D$ −47.4° (chloroform), can be obtained in similar manner using (−) α-phenylethanol.

PREPARATION 9

1.0 G. of 2-(5-oxo-5H-dibenzo[a,d]cyclohepten-2-yl)propionic acid is dissolved in 25 ml. of chloroform, and 1 ml. of thionyl chloride and 0.1 ml. of diethylformamide are added thereto. The mixture is left for 1 hour then evaporated under high vacuum to afford 2-(5-oxo-5H-dibenzo[a,d]cyclohepten-2-yl)propionyl chloride. In similar manner, substituting the acids prepared in Preparations 3 and 5–8 for the 2-(5-oxo-5H-dibenzo[a,d]cyclohepten-2-yl)propionic acid used above, the corresponding acid chlorides are prepared.

EXAMPLE 1

0.5 G. of 2-(5-oxo-5H-dibenzo[a,d]cyclohepten-2-yl)propionyl chloride is dissolved in 25 ml. of acetonitrile containing 0.5 ml. of allyl alcohol and 0.5 ml. of triethylamine. After 16 hours the mixture is evaporated to dryness and partitioned between ethyl acetate and water. The organic solution is washed, dried, passed through a short (10 g.) silica gel column, then evaporated to give allyl 2-(5-oxo-5H-dibenzo[a,d]cyclohepten-2-yl)propionate as an oil [nmr spectrum in deuterochloroform relative to tetramethylsilane: 1.54 (doublet, CH₃), 2.84 (quartet, CH), 4.55 (doublet, OCH₂), 5.1–6.0 (multiplet, CH=CH₂) and 7.00 ppm (singlet, 10, 11-H); mass spectrum: 318(M+) 233,205].

In a similar manner, substituting the other acid chlorides of Preparation 9 for the 2-(5-oxo-5H-dibenzo[a,d]cyclohepten-2-yl)-propionyl chloride used above, the corresponding allyl esters are prepared, including allyl (5-oxo-5H-dibenzo[a,d]cyclohepten-2-yl)acetate, allyl 2-(5-oxo-5H-dibenzo[a,d]cyclohepten-2-yl)butyrate and allyl 2-(5-oxo-5H-dibenzo[a,d]cyclohepten-2-yl)acrylate.

EXAMPLE 2

0.5 G. of 2-(5-oxo-5H-dibenzo[a,d]cyclohepten-2-yl)propionyl chloride is dissolved in 25 ml. of acetonitrile containing 0.5 ml. of 2,3-epoxypropan-1-ol and 0.5 ml. of triethylamine. After 16 hours the solution is added to water and extracted with ethyl acetate. The extract is washed, dried, passed through a short (10 g.) silica gel column and evaporated to afford 2′, 3′-epoxyprop-1′-yl 2-(5-oxo-5H-dibenzo[a,d]cyclohepten-2-yl)propionate as an oil [nmr spectrum in deuterochloroform relative to tetramethylsilane: 1.57 (doublet, $CH_3$), 2.4–3.2, 3.7–4.6 (multiplets) and 7.02 ppm; mass spectrum: 334 (M+) 318, 306, 233, 205].

In similar manner, substituting the other acid chlorides of Preparation 9 for the 2-(5-oxo-5H-dibenzo[a,d]cyclohepten-2-yl)propionyl chloride used above, the corresponding 2′, 3′-epoxyprop-1′-yl esters are prepared, including 2′, 3′-epoxyprop-1′-yl (5-oxo-5H-dibenzo[a,d]cyclohepten-2-yl)acetate, 2′,3′-epoxyprop-1′-yl 2-(5-oxo-5H-dibenzo[a,d]cyclohepten-2-yl)butyrate, and 2′,3′-epoxyprop-1′-yl 2-(5-oxo-5H-dibenzo[a,d]cyclohepten-2-yl)acrylate.

EXAMPLE 3

0.5 G. of d 2-(5-oxo-5H-dibenzo[a,d]cyclohepten-2-yl)propionic acid is stirred for 2 hours in 15 ml. of methylene chloride containing 1 ml. of thionyl chloride and 1 drop of dimethylformamide. The solution is evaporated to dryness, and the residue dissolved in 10 ml. of dry benzene, then re-evaporated. A solution of 3 ml. of dl 4-hydroxymethyl-2,2-dimethyl-1,3-dioxolane and 1 ml. of pyridine in 15 ml. of tetrahydrofuran is added to the residue. After 72 hours the mixture is added to water and extracted with ether. The ethereal solution is washed, dried and evaporated to afford the ester of dl 4-hydroxymethyl-2,2-dimethyl-1,3-dioxolane with d 2-(5-oxo-5H-dibenzo[a,d]cyclohepten-2-yl)propionic acid, m.p. 60°–75°; $[\alpha]_D = +12.4°$ (10 mg/ml, ethyl acetate).

In similar manner, substituting d 4-hydroxymethyl-2,2-dimethyl-1,3-dioxolane for the corresponding dl reactant used above, there is obtained the ester of d 4-hydroxymethyl-2,2-dimethyl-1,3-dioxolane with d 2-(5-oxo-5H-dibenzo[a,d]-cyclohepten-2-yl)propionic acid, m.p. 68°–70°; $[\alpha]_D = +14.7°$ (10 mg/ml, ethyl acetate).

Also in similar manner, substituting the acids of Preparations 3, 5 and 6 above for the d 2-(5-oxo-5H-dibenzo[a,d]cyclohepten-2-yl)propionic acid, the corresponding esters are prepared, including (2,2-dimethyl-1,3-dioxolan-4-yl)methyl (5-oxo-5H-dibenzo[a,d]cyclohepten-2-yl)acetate, (2,2-dimethyl-1,3-dioxolan-4-yl)methyl 2-(5-oxo-5H-dibenzo[a,d]cyclohepten-2-yl)butyrate, and (2,2-dimethyl-1,3-dioxolan-4-yl)methyl 2-(5-oxo-5H-dibenzo[a,d]cyclohepten-2-yl)acrylate.

Also in similar manner, substituting 4hydromethyl-2-methyl-1,3-dioxolane, 4-hydroxymethyl-2-hexyl-1,3-dioxolane, 4-hydroxymethyl-1,3-dioxolane, 4-hydroxymethyl-2-phenyl-1,3-dioxolane, 4-hydroxymethyl-2-benzyl-1,3-dioxolane, 4-hydroxymethyl-2,2-(1,4-tetramethylene)-1,3-dioxolane, 4-hydroxymethyl-2,2-(1,5-pentamethylene)-1,3-dioxolane, or 4-hydroxymethyl-2,2-(1,6-hexamethylene)-1,3-dioxolane for the 4-hydroxymethyl-2,2-dimethyl-1,3-dioxolane used above, the corresponding esters are prepared, including (2-methyl-1,3-dioxolan-4-yl)methyl 2-(5-oxo-5H-dibenzo[a,d]cyclohepten-2-yl)propionate, (2-hexyl-1,3-dioxolan-4-yl)methyl 2-(5-oxo-5H-dibenzo[a,d]cyclohepten-2-yl)propionate, (1,3-dioxolan-4-yl)methyl 2-(5-oxo-5H-dibenzo[a,d]cyclohepten-2-yl)propionate, (2-phenyl-1,3-dioxolan-4-yl)methyl 2-(5-oxo-5H-dibenzo[a,d]cyclohepten-2-yl)propionate, (2-benzyl-1,3-dioxolan-4-yl)methyl 2-(5-oxo-5H-dibenzo[a,d]cyclohepten-2-yl)propionate, [2,2-(1,4-tetramethylene)-1,3-dioxolan-4-yl]methyl 2-(5-oxo-5H-dibenzo[a,d]cyclohepten-2-yl)propionate, [2,2-(1,5-pentamethylene)-1,3-dioxolan-4-yl]methyl 2-(5-oxo-5H-dibenzo[a,d]cyclohepten-2-yl)propionate, and [2,2-(1,6-hexamethylene)-1,3-dioxolan-4-yl]methyl 2-(5-oxo-5H-dibenzo[a,d]cyclohepten-2-yl)propionate.

EXAMPLE 4

1.37 G. of the ester of d 4-hydroxymethyl-2,2-dimethyl-1,3-dioxolane with d 2-(5-oxo-5H-dibenzo[a,d]cyclohepten-2-yl)propionic acid (as prepared in Example 3 above) is stirred for 16 hours in 30 ml of acetone and 10 ml of 10% hydrochloric acid. The mixture is poured into water and extracted with ether. The extract is washed, dried and evaporated. The residue is recrystallized from ethyl acetate/hexane to afford 2′ (R), 3′-dihydroxy-prop-1′-yl d 2-(5-oxo-5H-dibenzo[a,d]cyclohepten-2-yl)propionate, m.p. 112°–114°; $[\alpha]_D = +66.7°$ (5 mg/ml, ethyl acetate).

In a similar manner, substituting the corresponding esters of Example 3 for the ester starting material used above, the corresponding 2′,3′-dihydroxyprop-1′-yl esters are prepared, including 2′,3′-dihydroxyprop-1′-yl (5-oxo-5H-dibenzo[a,d]cyclohepten-2-yl)acetate, 2′,3′-dihydroxyprop-1′-yl 2-(5-oxo-5H-dibenzo[a,d]cyclohepten-2-yl)propionate, 2′,3′-dihydroxyprop-1′-yl 2-(5-oxo-5H-dibenzo[a,d]cyclohepten-2-yl)butyrate, and 2′,3′-dihydroxyprop-1′-yl 2-(5-oxo-5H-dibenzo[a,d]cyclohepten-2-yl)acrylate.

EXAMPLE 5

0.5 Ml. of pyridine is added to 2.0 ml of a 12% solution of phosgene in benzene at 0° C. A solution of 0.25 g. of 2′ (R), 3′-dihydroxyprop-1′-yl d 2-(5-oxo-5H-dibenzo[a,d]cyclohepten-2-yl)propionate (as prepared in Example 4) in 1.5 ml of dioxane is then added. The mixture is left at room temperature for 16 hours then added to water and ethyl acetate. The organic solution is washed, dried and evaporated to give (2-oxo-1,3-dioxolan-4(S)-yl)methyl d 2-(5-oxo-5H-dibenzo[a,d]cyclohepten-2-yl)propionate as a gum; nmr spectrum in deuterochloroform relative to tetramethylsilane: 1.56 (doublet, $CH_3$), 2.87 (quartet, CH) and 7.01 ppm (singlet, 10,11-H); infrared spectrum 1800, 1730 cm.$^{-1}$; $[\alpha]_D + 3.0°$ (5mg/ml, ethyl acetate);

In similar manner substituting the other ester starting materials prepared in Example 4 for the ester starting material used above, the corresponding esters are prepared, including (2-oxo-1,3-dioxolan-4-yl)methyl (5-oxo-5H-dibenzo[a,d]cyclohepten-2-yl)acetate, (2-oxo-1,3-dioxolan-4-yl)methyl 2-(5-oxo-5H-dibenzo[a,d]cyclohepten-2-yl)propionate, (2-oxo-1,3-dioxolan-4-yl)methyl 2-(5-oxo-5H-dibenzo[a,d]cyclohepten-2-yl)butyrate, and (2-oxo-1,3-dioxolan-4-yl)methyl 2-(5-oxo-5H-dibenzo[a,d]cyclohepten-2-yl)acrylate.

EXAMPLE 6

0.25 G. of 2' (R), 3'-dihydroxy-prop-1'-yl d 2-(5-oxo-5H-dibenzo[a,d]cyclohepten-2-yl)propionate (as prepared in Example 4) is refluxed for 30 minutes in 5 ml of toluene containing 0.2 g. of thiocarbonyldiimidazole. The solution is cooled, diluted with ethyl acetate and washed, dried and evaporated. The residue is chromatographed on silica gel, eluting with ethyl acetate-hexane (3:2) to afford (2-thioxo-1,3-dioxolan-4 (S)-yl)methyl d 2-(5-oxo-5H-dibenzo[a,d]cyclohepten-2-yl)propionate as an oil; mass spectrum: 394 (M+), 350.

In similar manner, substituting the other ester starting materials prepared in Example 4 for the ester starting material used above, the corresponding esters are prepared, including (2-thioxo-1,3-dioxolan-4-yl)methyl (5-oxo-5H-dibenzo[a,d]cyclohepten-2-yl)acetate, (2-thioxo-1,3-dioxolan-4-yl)methyl 2-(5-oxo-5H-dibenzo[a,d]cyclohepten-2-yl)propionate, (2-thioxo-1,3-dioxolan-4-yl)methyl 2-(5-oxo-5H-dibenzo[a,d]cyclohepten-2-yl)butyrate, and (2-thioxo-1,3-dioxolan-4-yl)methyl 2-(5-oxo-5H-dibenzo[a,d]cyclohepten-2-yl)acrylate.

EXAMPLE 7

A solution is prepared having 10 mg. of the ester of 4-hydroxymethyl-2,2-dimethyl-1,3-dioxolane with d 2-(5-oxo-5H-dibenzo[a,d]cyclohepten-2-yl)propionic acid dissolved per ml. of solution of 70% ethanol and 30% simple syrup (U.S.P.).

EXAMPLE 8

A solution is prepared having 10 mg. of the ester of d 4-hydroxymethyl-2,2-dimethyl-1,3-dioxolane with d 2-(5-oxo-5H-dibenzo[a,d]cyclohepten-2-yl)propionic acid per ml. of solution of 70% ethanol and 30% simple syrup (U.S.P.).

EXAMPLE 9

A suspension is prepared having 10 mg. of the ester of 4-hydroxymethyl-2,2-dimethyl-1,3-dioxolane with d 2-(5-oxo-5H-dibenzo[a,d]cyclohepten-2-yl)propionic acid per ml. of normal saline solution.

The suspension prepared above can optionally include 0.1% Tween 80 (sorbitan monooleate polyoxyethylene; a product of Atlas Chemical Industries, Inc.)

EXAMPLE 10

| Ingredients | Quantity per tablet, mgs. |
|---|---|
| The ester of d 4-hydroxymethyl-2,2-dimethyl-1,3-dioxolane with d 2-(5-oxo-5H-dibenzo[a,d]cyclohepten-2-yl)propionic acid | 30 |
| cornstarch (paste) | 25 |
| magnesium stearate | 0.4 |
| lactose | to 250 |

The above ingredients are thoroughly mixed and pressed into single scored tablets.

EXAMPLE 11

| Ingredients | Quantity per tablet, mgs. |
|---|---|
| The ester of 4-hydroxymethyl-2,2-dimethyl-1,3-dioxolane with d 2-(5-oxo-5H-dibenzo[a,d]cyclohepten-2-yl) propionic acid | 25 |
| cornstarch | 19 |
| magnesium stearate | 0.4 |
| polyvinylpyrrolidone | 8 |
| lactose | 190 |

The above ingredients are thoroughly mixed and pressed into single scored tablets.

EXAMPLE 12

| Ingredients | Quantity per capsule, mgs. |
|---|---|
| The ester of 4-hydroxymethyl-2,2-dimethyl-1,3-dioxolane with d 2-(5-oxo-5H-dibenzo[a,d]cyclohepten-2-yl)propionic acid | 25 |
| cornstarch | 20 |
| lactose | to 200 |

The above ingredients are mixed and introduced to a hardshell gelatin capsule.

EXAMPLE 13

| Ingredients | Quantity per capsule, mgs. |
|---|---|
| The ester of d 4-hydroxymethyl-2,2-dimethyl-1,3-dioxolane with d 2-(5-oxo-5H-dibenzo-[a,d]cyclohepten-2-yl)propionic acid | 30 |
| lactose | 72 |
| magnesium stearate | 8 |

The above ingredients are mixed and introduced to a hardshell gelatin capsule.

EXAMPLE 14

A suppository totaling 2.8 grams is prepared having the following composition:

| | |
|---|---|
| The ester of d 4-hydroxymethyl-2,2-dimethyl-1,3-dioxolane with d 2-(5-oxo-5H-dibenzo[a,d]cyclohepten-2-yl)propionic acid | 10–50 mg. |
| Witepsol H-15 (triglycerides of saturated vegetable fatty acids; a product of Riches-Nelson, Inc. New York, N.Y. | balance |

EXAMPLE 15

The anti-inflammatory activity of the following compounds embraced within this invention was compared with the activity of phenylbutazone by means of the carrageenin-induced rat paw inflammation test described below.

TEST FOR ANTI-INFLAMMATORY ACTIVITY UTILIZING CARRAGEENIN INDUCED PAW INFLAMMATION IN THE RAT

Materials and Methods — Female rats weighing 80–90 grams are used. The test materials are given at hour 0 orally by gavage in 1 ml. aqueous vehicle. At hour 1, 0.05 ml. of a 1% solution (in 0.9% NaCl) of carrageenin is injected into the right hind paw. This injection causes an inflammation of the paw. The rats are sacrificed at hour 4, at which time both hind paws are removed and weighed separately.

End point: % increase in paw size calculated as follows:

$$\frac{\text{Wt. of Right Paw} - \text{Wt. of Left Paw}}{\text{Wt. of Left Paw}} \times 100$$

The results of these tests are summarized in the following table:

| Compound | Oral Anti-Inflammatory Activity (Phenylbutazone = 1) |
|---|---|
| The ester of 4-hydroxymethyl-2, 2-dimethyl-1,3-dioxolane with d 2-(5-oxo-5H-dibenzo-[a,d]cyclohepten-2-yl) propionic acid | 45 |
| The ester of d 4-hydroxymethyl-2, 2-dimethyl-1,3-dioxolane with d 2-(5-oxo-5H-dibenzo-[a,d]cyclohepten-2-yl)-propionic acid | 55 |
| 2',3'-epoxyprop-1'-yl 2-(5-oxo-5H-dibenzo-[a,d]cyclohepten-2-yl)propionate | 12 |
| allyl 2-(5-oxo-5H-dibenzo[a,d]cyclohepten-2-yl)propionate | 12 |
| 2'(R),3'-dihydroxy-prop-1'-yl d 2-(5-oxo-5H-dibenzo[a,d]cyclohepten-2-yl)propionate | ~40 |

While the present invention has been described with reference to specific embodiments thereof, it should be understood by those skilled in this art that various changes may be made and equivalents may be substituted without departing from the true spirit and scope of the invention. In addition, many modifications can be made to adapt a particular situation, material or composition of matter, process, process step or steps, or then-present objective to the spirit of this invention without departing from its essential teachings.

What is claimed is:

1. A compound selected from the group of compounds represented by the formula:

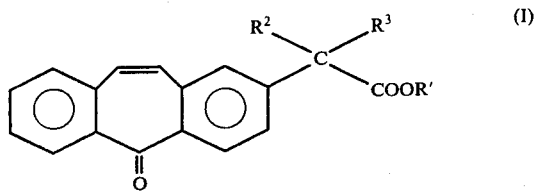

where R' is

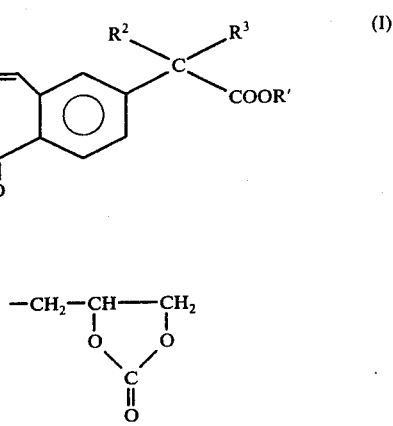

one of $R^2$ and $R^3$ is hydrogen and the other is methyl.

2. The compound of claim 1 wherein said compound is (2-oxo-1,3-dioxolan-4(S)-yl)methyl d 2-(5-oxo-5H-dibenzo[a,d]cyclohepten-2-yl)propionate.

3. A composition for treating inflammation, pain or pyrexia in mammals comprising a pharmaceutically acceptable non-toxic excipient and a therapeutically effective amount of a compound represented by the formula:

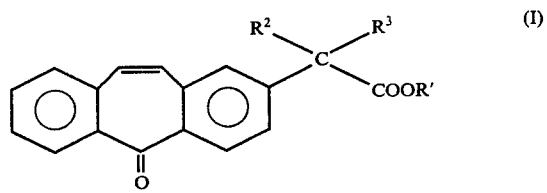

where R' is

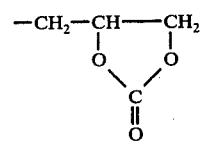

one of $R^2$ and $R^3$ is hydrogen and the other is methyl.

4. The composition of claim 3 wherein said compound is (2-oxo-1,3-dioxolan-4(S)-yl)methyl d 2-(5-oxo-5H-dibenzo[a,d]cyclohepten-2-yl)propionate.

* * * * *